United States Patent [19]

Janssen

[11] Patent Number: 4,694,683

[45] Date of Patent: Sep. 22, 1987

[54] METHOD TO AUTOMATICALLY DETERMINE THE SIZE DISTRIBUTION OF SHIVE AND ANALYZER THEREFOR

[75] Inventor: Wladmir Janssen, Montreal, Canada

[73] Assignee: Domtar Inc., Montreal, Canada

[21] Appl. No.: 828,344

[22] Filed: Feb. 11, 1986

[51] Int. Cl.$^4$ .................................... G01N 15/06
[52] U.S. Cl. ................................................ 73/63
[58] Field of Search ............................ 73/63, 61 R

[56] References Cited

U.S. PATENT DOCUMENTS

| 3,893,334 | 7/1975 | Williams | 73/63 X |
| 4,399,691 | 8/1983 | Janssen | 73/63 |
| 4,554,051 | 11/1985 | Danforth | 73/63 X |

FOREIGN PATENT DOCUMENTS

| 224675 | 7/1985 | German Democratic Rep. | 73/63 |
| 1100128 | 1/1968 | United Kingdom | 73/63 |

*Primary Examiner*—Stewart J. Levy
*Assistant Examiner*—Joseph W. Roskos

[57] ABSTRACT

An apparatus to automatically determine on-line, the shive content and shive size distribution of a wood pulp: The apparatus includes a line having an inlet and outlet, and a plug for closing the line. A motor and gear displaces the line with respect to the plug for defining a gap. A transducer measures the size of the gap. A sensor monitors impedances in the line caused by the accumulation of oversized shives at the gap. Responsive to the sensor, is a device for releasing the impedance by rapidly enlarging the gap, each release during a time period being registered by a counter. A controller correlates each of the counts with the corresponding size of gap to establish the content and size distribution of the shives. The method comprises passing through a measured variable gap a measured flow of wood pulp, measuring the pressure increase caused by the shives exceeding the size of the gap, enlarging the gap to allow the passage of all shives when the pressure has reached a predetermined level, repeating the same while automatically varying the size of the gap and registering over time the number of occurrences the gap is enlarged for each gap size and correlating the number of occurrences and the sizes of gap to automatically determine on-line the shive content and shive size distribution.

10 Claims, 5 Drawing Figures

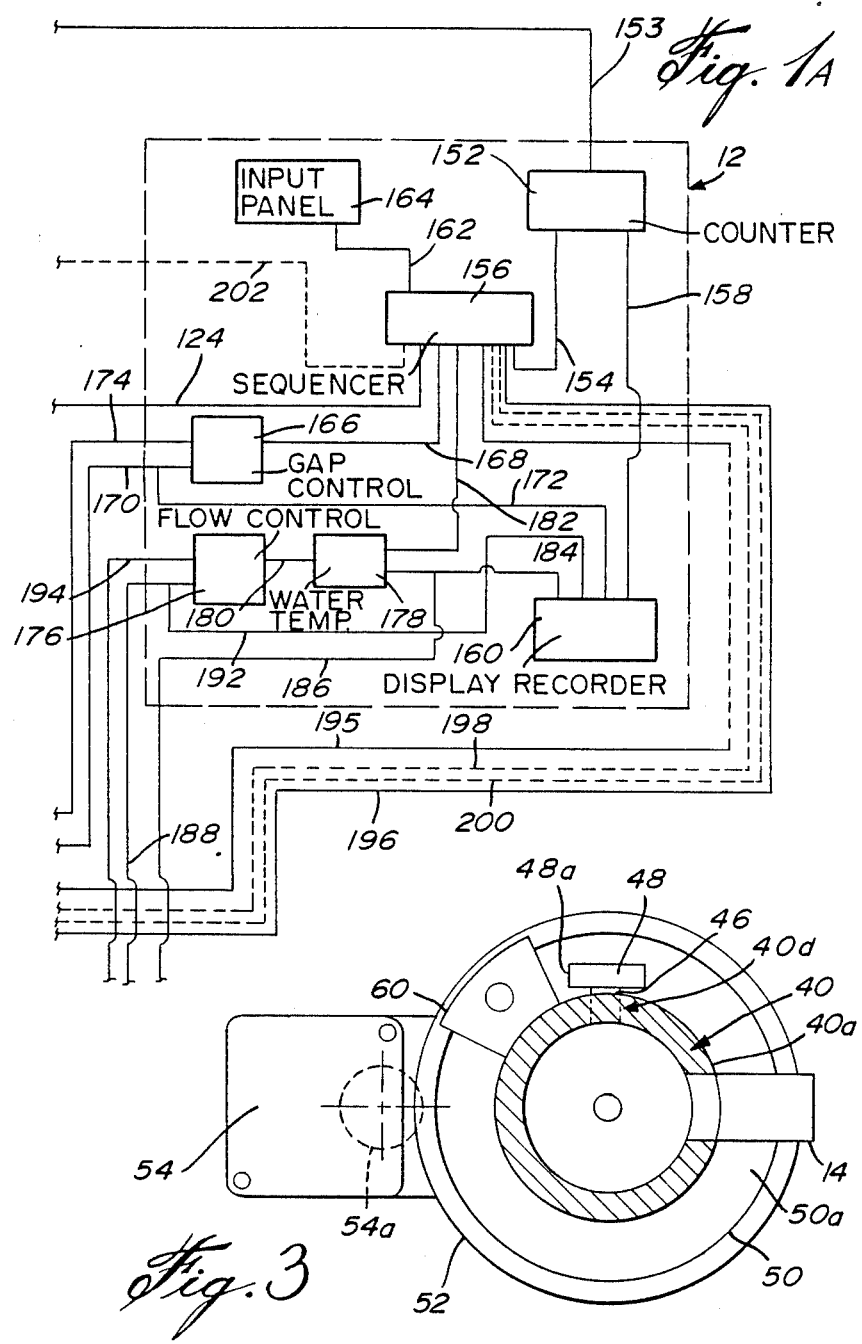

[4,694,683]

METHOD TO AUTOMATICALLY DETERMINE THE SIZE DISTRIBUTION OF SHIVE AND ANALYZER THEREFOR

FIELD OF THE INVENTION

This invention relates to a shive analyzer for determining the shive content and the size distribution of the shives in a wood pulp, and a method of carrying out same. More particularly, this invention relates to an automatic shive analyzer which monitors on-line, a shive size distribution in the wood pulp.

BACKGROUND OF THE INVENTION

Techniques are available to the pulp and paper industry to determine the shive content in a pulp. Each focuses on shives of a particular size. One of the techniques as disclosed in U.S. Pat. No. 4,342,618 invented by Karnis et al, involves the use of screens. Another technique as disclosed in U.S. Pat. No. 4,399,691 invented by Janssen and assigned to the present assignee, involves the use of a gap.

In each technique, the size of the retained or trapped fibres is slightly larger than the mesh or the gap. The resulting fibre content calculation, therefore, is based on a given size of fibres, that are slightly larger than the size of the mesh or the gap. In many cases however, a series of fibre content calculations over a particular range of fibre sizes would yield more important information as to the condition of the prepared pulp. With present techniques, such a series would require the use of a number of different sized meshes or gaps, resulting in a long and expensive procedure.

In addition, a continuous monitoring of a range in fibre sizes, or a fibre size distribution, would greatly improve the analysis of wood pulp. This is especially so in the paper making processes that practise a continuous treatment of the wood pulp. Present techniques however, are insufficient in a continuous monitoring mode due to high labour requirements and overly long cycle time periods. Furthermore, characteristics of the pulp fibre must be assumed constant on these long cycle time periods, and therefore leading to further inaccuracies.

BRIEF DESCRIPTION OF THE PRESENT INVENTION

It is, therefore, an object of the present invention to provide a device to automatically and continuously monitor on-line, the fibre size distribution of a wood pulp.

Broadly stated, the invention comprises an apparatus to automatically determine on-line, the shive content and shive size distribution of a wood pulp; said apparatus comprising a line having an inlet for receiving a flow of wood pulp containing shives and an outlet whereby said flow of pulp is leaving said line, a plugging means for closing said line, a means to automatically displace said plugging means, as to gradually increase, or decrease a gap between said line and said plugging means, and responsive to said means automatically displacing said plugging means, a means translating and recording the size of said gap, said gap allowing during operating conditions, the passage of the flow of wood pulp and the portion of shives having less than the size of said gap at a given moment, while temporarily preventing the passage of shives exceeding the size of said gap and thereby interfering with the flow of wood pulp through the gap and thereby through said lines, thereby causing impedance in said lines, a sensing means for monitoring the impedance in said line over a predetermined threshold level, and responsive to said means of sensing impedance over said threshold level, a means for rapidly releasing said plugging means whereby upon each occurrence of said threshold over said predetermined level, said impedance sensing means actuates said rapidly releasing means and thereby instantaneously enlarge said gap from said operating conditions as to permit the passage therethrough of said portion of shives, exceeding the size of the gap, and a short period of time thereafter, rapidly returning said closing means and said gap to said operating conditions, and responsive to said rapidly releasing means, a means for registering said occurrence of said impedance over said threshold level during a predetermined period of time, a means responsive to said registering means and said means for measuring the gap size, to correlate said counts to the size of said gap indicative of the size distribution of said shives, and a means characterizing the flow of wood pulp in said inlet of said line, said characterizing means being selected from one means selected from pressure measuring means, volume means, pressure regulating means, volume regulating means.

The method comprises passing through a variable gap a measured flow of wood pulp measuring the size of the gap, measuring the pressure increase indicative of the number of shives exceeding the size of said gap, enlarging the gap to allow the passage of all shives when the pressure has reached a predetermined level, repeating the same while automatically varying the size of said gap and registering overtime the number of occurrences the gap is enlarged versus the sizes of the gap and correlating said registering of number of occurrences and said sizes of gap indicative of the size distribution of the shive.

In a particular embodiment, said means for closing said line is a plug and at least one wall disposed therearound, said displacing means is a guide to align said at least one wall with said plug and to displace said plug with respect to said at least one wall, thereby forming said gap, defined by the surface of said plug and the inner face of said at least one wall, said means to vary said displacing means is a threaded portion for engaging a rotational drive source with said guide.

By the term "impedance" is generally meant the interference in a line containing a flow of liquid, caused by the particles entrained therein and generally resulting in an increase in pressure or a decrease in flow rate or a combination thereof in said line.

By the term "shive size" is generally meant a dimensional description of the shives taking into account the mean width thereof.

By the term "size of said gap" is generally meant a dimensional description of the gap taking into account its mean width, thereby substantially corresponding to the "shive size".

BRIEF DESCRIPTION OF THE DRAWINGS

Further features, objects and advantages will be evident in the following detailed description of a preferred embodiment of the present invention taken in conjunction with the accompanying drawings in which:

FIGS. 1 and 1A combine to form a schematic and cross-sectional view of the general assembly of an automatic shive analyzer with a linear variable displacement transducer rotated to improve illustration.

FIG 1A is the automatic control portion of the automatic shive analyzer and illustrates one of the means for counting the occurrence of threshold level, and one of the means responsive to said counting means for measuring the gap size and to correlate the counts to the size of the gap indicative of the size of the shive.

FIG. 3 is a cross-sectional view of the line closing assembly with respect to line 3—3 of FIG. 1.

Referring to FIG. 1, the automatic shive analyzer 10 has a mechanical outlet portion shown at 11, an automatic control portion generally shown at 12 (FIG. 1a) and a supply portion shown at 13 (lower portion of FIG. 1).

First, to be discussed is the mechanical outlet portion 11 (upper portion of FIG. 1) which comprises a line 14 whose one end is flexibly connected to the line closing assembly 15, to be described, and whose other end is flexibly connected to an impedance sensing assembly 16 to be described.

Figure 2:
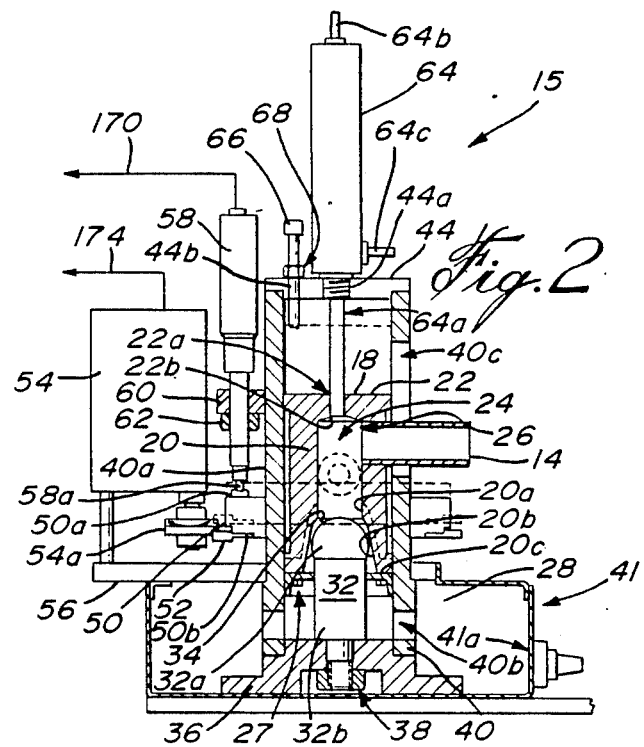
FIG. 2 is an enlarged cross-sectional view of the line closing assembly shown in FIG. 1.

As shown in FIG. 2, the line closing assembly 15 comprises an inverted elongated cylindrical cup 18 having a cylindrical body section 20 with an upper inner wall face 20a and a lower inner wall face 20b. Fused onto one end of cylindrical body section 20 and thereby forming cylindrical cup 18 is a wall forming top wall 22. A threaded hole 22a is machined into the upper surface of top wall 22 to receive the piston of an actuating device to be described.

Defined by inner face 22b of the top wall 22 and the upper inner face 20 a of cylindrical body section 20 is closure chamber 24. Located near the top wall 22 and formed by the removal of a walled portion from cylindrical body section 20 is aperture 26 which links the outside with closure chamber 24 and therefore defines an inlet, to receive the attachment of line 14 thereto.

At the lower end of elongated cylindrical cup 18, end face 20c is machined for the attachment of a cup seal 27 by means of fasteners. Located near lower end face 20c of elongated cylindrical cup 18 and defined by the wall of the cylindrical body section 20 is aperture 28 which links the closure chamber 24 with the outside and therefore defining an outlet.

Lower inner face 20b of the cylindrical section is machined to a conical shape with the inner diameter thereof decreasing inwardly from outlet 28. The lower inner wall is so disposed as to receive plug 32 defining a means for closing line 14 and having a spherical upper section 32a and a cylindrical lower section 32b. The insertion of the spherical upper section 32a in the outlet 28 produces an annular gap 34 defined by the spherical upper section 32a and the lower inner face 20b.

If desired, other arrangements may be used to close line 14 including cone, disc or other shaped elements which co-act with the line or as seat portion to define a gap, as is known to those skilled in the art.

Plug 32 is fixably mounted on base frame 36 by means of cylindrical lower section 32b and bolt arrangement 38. Fused to base frame 36 is guide frame 40 of cylindrical cross-section in which slides elongated cylindrical cup 18. Guide frame 40 aligns the central axis of the elongated cylindrical cup 18 with the central axis of the spherical plug 32. The outer face 40a of guide 40 is machined to provide a threaded portion for receiving an annular ring to be described.

A plurality of equally spaced holes are formed in the lower most region of guide frame 40 to form apertures shown at 40b therein defining closure assembly outlets for the outflow of wood pulp. A first narrow elongated walled portion is removed from the guide frame 40 to form first elongated guide aperture 40c thereby permitting both the sealable attachment of the line 14 to the inlet 26 of the cylindrical cup 18 and the sliding of cylindrical cup 18 in guide frame 40. A second elongated walled portion is removed from the guide frame to form second elongated guide aperture 40d (better shown in FIG. 3) for the attachment of a bar to be discussed. Surrounding the lower region of guide frame 40, containing therein closure assembly outlets 40b, is pulp collection reservoir 41 having a reservoir outlet 41a, to which is sealably coupled return line 42 (better shown in FIG. 1).

Mounted on the upper end of cylindrical guide frame 40 by means of threaded fasteners is end cap 44, which has two circular walled portions removed therefrom to form first aperture 44a for the passage therethrough of an actuating rod and second aperture 44b which is threaded to receive a setting screw, both to be described. Radially fixedly mounted to outer face of cylindrical body section 20 and posed perpendicular with respect to the longitudinal axis of elongated cylindrical cup 18 is stopper bar 46 (better shown in FIG. 3), which passes through second guide aperature 40d. Fixedly mounted to the unattached end of stopper bar 46 is the inner race of bearing 48 whose axis of rotation is parallel with respect to the central axis of stopper bar 42. In rolling contact with bearing outer race 48a and threadably engaged to the outside threaded face 40a of guide frame 40 is annular ring 50 whose upper radially oriented face 50a provides a rolling surface for outer race 48a. If desired, other arrangements may be used to displace the closing means including a guide frame to slidably mount plug 32 with respect to cylindrical cup 18.

Fixedly mounted to the bottom radially oriented face 50b of annular ring 50 is annular gear 52. Meshing with annular gear ring 52 is the drive gear 54a of drive motor 54 which is adjustably mounted on drive motor base 56 with threaded fasteners. Drive motor 54 rotates annular ring 50 via drive gear 54a and consequently varies the displacing means.

Drive gear 54a is of sufficient thickness or multiple to allow it to remain engaged with annular ring 50 as the latter moves up or down. If desired, ratchet arrangements may also be used to displace the closing means. For example, the linear motion of a push-pull solenoid may translate into rotary motion to rotate annular ring 50.

Other means to adjust the gap size are also contemplated as are known to those skilled in the art.

Adjustably attached on the guide frame 40 is linear displacement transducer 58 which is aligned with annular ring 50 by means of transducer frame 60 (better shown in FIG. 2) and threaded locking nut 62. Piston 58a extends from transducer 58 and is in sliding contact with the upper radially oriented face 50a of annular ring 50, to register the displacement of annular ring 50 and thereby the size of gap 34.

Also contemplated to register the size of the gap 34 are devices to measure the rotation of annular ring 50. For instance, a "step" motor with the appropriate controls or a shaft encoder may be used, as is known, to measure the rotational displacement of annular ring 50.

Fixedly mounted on cylinder end cap 44, by means of a frame not shown, is pneumatic piston actuator 64 whose piston 64a is passed through first aperture 44a and threadibly engaged with threaded hole 22a of elongated cylindrical cup 18. Air passage lines 64b and 64c are coupled to a four-way valve for the rapid release of cylindrical cup 18, to be described. Inserted through second aperture 44b is setting screw 66 for presetting the travel of cylindrical cup 18, which is adjusted by means of adjusting ring or nut 68.

Although not preferred, a solenoid type piston actuator may be used in lieu of pneumatic piston actuator 64 as a means for rapidly releasing cylindrical cup 18.

Having described in detail the closure assembly 15 of the mechanical outlet portion 11, the impedance sensing assembly 16 will now be discussed.

Figure 1:
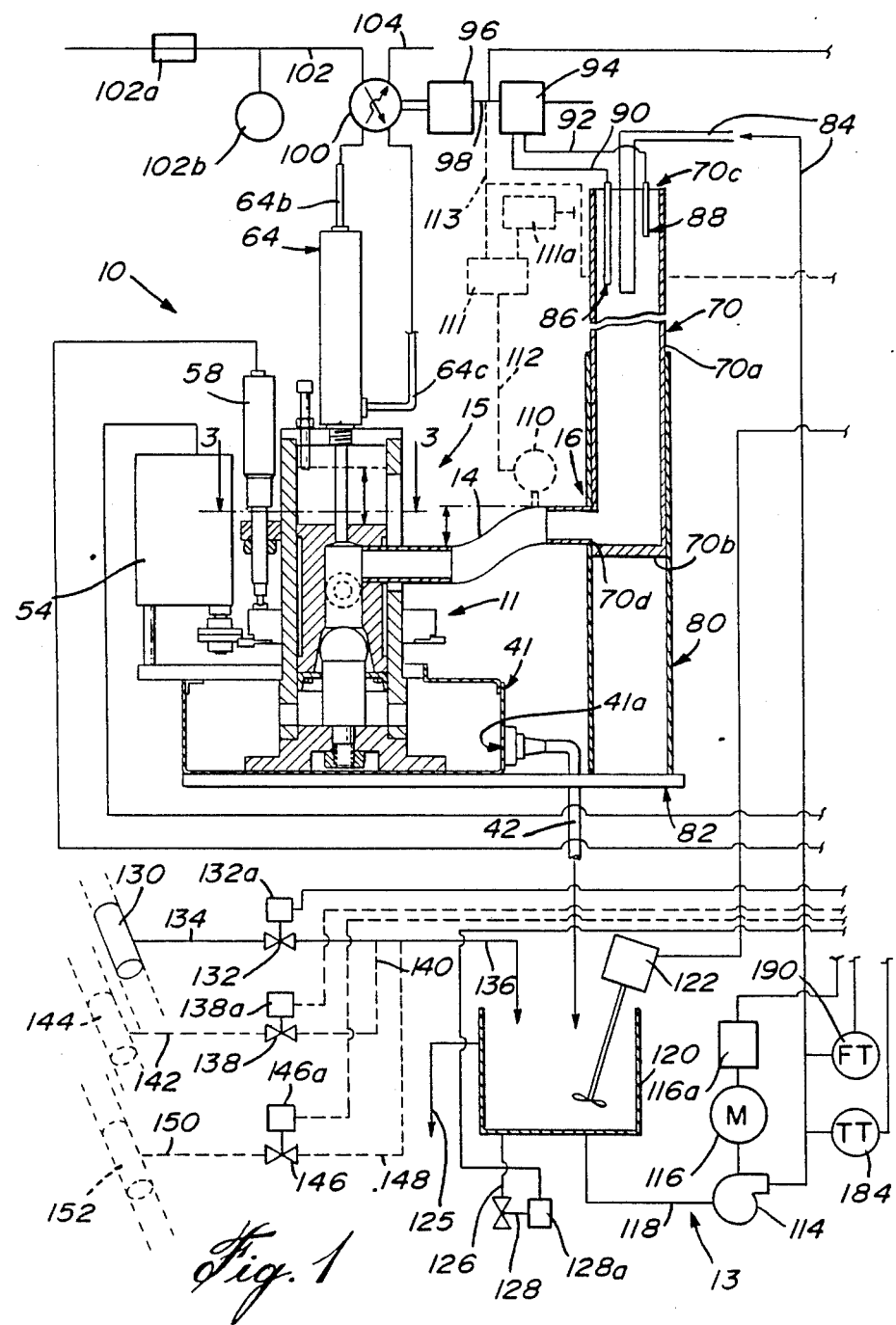

Referring to FIG. 1, the impedance sensing assembly 16 comprises an elongated stand pipe 70 for containing a column of pulp and is constructed from pipe section 70a preferably of a transparent plastic material. Fused onto the bottom end of transparent pipe section 70a is end cap 70b. The opposite upper end of pipe section 70a remains open and defines the stand pipe inlet 70c. A walled portion is removed from transparent pipe section 70a near the end cap 70b to form aperture 70d and to define the stand pipe outlet for the coupling of line 14 thereto. Stand pipe 70 is joined to pipe section frame 80 which is oriented parallel with respect to gravity and fused to base 82.

Positioned through the inlet 70c of the stand pipe and rigidly mounted on a frame not shown is inlet line 84 for pulp delivery to the stand pipe 70. Also positioned through the inlet 70c of the stand pipe and adjustably mounted on a frame not shown are low and high height sensing electrodes 86 and 88 respectfully. These generate signals, upon contact with the pulp, which are conveyed by conductors 90 and 92 respectfully to level switch 94, (such as those manufactured by Amprotek, Pointe Claire, Quebec). Level switch 94 generates signals depending on the conditions in the stand pipe as indicated by low and high height sensing electrodes 86 and 88, respectively. The signals from the level switch 94 are received by solenoid 96 via conductor 98. In response, solenoid 96 actuates four-way release valve 100 to rapidly raise and subsequently lower cylindrical cup 18. Valve 100 is operatively coupled with a pneumatic supply line 102, atmospheric release line 104, and air passage lines 64b and 64c of pneumatic piston actuator 64. Generally, such pneumatic supply lines are equipped with pressure regulator 102a and gauge 102b. "Characterizing the flow of wood pulp" is obtained by means such as pressure measuring means, volume measuring means, pressure regulating means or volume regulating means.

Also contemplated for impedance sensing is pressure transducer 110, which is known to those skilled in the art, coupled to line 14 and enabling solenoid 96 via limit relay 111 and conductors 112 and 113 when the pressure in line 12 exceeds a preset limit value, adjustable by means of a dial or other adjustment 111a or by the automatic control portion 12 to be described.

Also contemplated for impedance sensing, in lieu of stand pipe 70, is a flow transmitter also shown at 110 which may generate signals pertaining to the flow rate in the line 14 as is known. These signals are conveyed to limit relay 111 via conductor 112 which in turn conveys a signal via conductor 113 to actuate relay 96 when the flow rate in line 12 is reduced beyond a preset limit value which may be adjusted by dial 111a or by automatic control portion 12, as will be described.

Having described the mechanical outlet portion 11 of the automatic shive analyzer, the supply portion 13 thereof will now be discussed.

Shown schematically, the inlet line 84 is coupled to the outlet of pump 114, which is driven by variable speed motor 116. Coupled to the inlet of pump 114 is line 118 which joins pump 114 to the outlet of agitation tank 120 which, in turn, receives pulp from return line 42. Positioned in agitation tank 120 is agitator 122 which is mounted on a frame not shown and actuated by automatic control portion 12 via conductor 124, as will be described.

If desired, agitation tank 120 may be eliminated by placing agitator 122 in reservoir 41 and providing reservoir 41 with the auxiliaries coacting with agitation tank 120.

Agitation tank 120 also includes overflow line 125 and drain line 126 which are used when flushing the system. Also joined to drain line 126 is solenoid actuated valve 128 which is actuated to drain agitation tank 120 or to flush the system.

Agitation tank 120 is further linked to supply line 130, for pulp delivery therefrom, by means of solenoid actuated valve 132 and lines 134 and 136. Also contemplated is the linking of agitation tank 120 with several supply pipe lines, as shown by solenoid actuated valve 138 and lines 140 and 142, joining line 136 with second supply pipe line 144, and solenoid actuated valve 146 and lines 148 and 150, joining line 136 with third supply pipe line 152.

If desired, pulp may be fed into stand pipe 70 or line 14 by means of a pulp reservoir positioned thereabove as is known to those skilled in the art. In this case, the flow rate of pulp entering standpipe 70 would depend on the elevation of the pulp with respect to the standpipe.

Having described the supply portion 13 of the automatic shive analyzer, attention will now be focused on the automatic control portion shown at 12 whose components are described hereinbelow.

Firstly, automatic control portion 12 has a counter 152 which receives input signals from the level switch 94 via conductor 98, 153. Counter 152 is periodically reset via conductor 154 by sequencer 156 and has an output which is connected via conductor 158 to display recorder 160 to record the "impedance" count as will be described. Display recorder 160 may be a chart recorder, a data logger or a microcomputer printer or plotter combination as is known to those skilled in the art.

Sequencer 156 is linked via conductor 162 to input panel 164 to receive various input parameters as will be described. Input panel 164 may have dials, switches, a keyboard or the like as is known.

Sequencer 156 coneys output signals to other components in a fixed time sequence, as will be described. These output signals are determined by the various input parameters conveyed by input panel 164. If desired, sequencer 156 may be based on a rotating cam assembly or other electromechanical device. Also, contemplated for sequencer 156 is electronic devices such as programmable logic controllers.

Sequencer 156 initiates the sequential functions of automatic control portion 12 including:

(i) the adjustment of the size of annular gap 34

(ii) the adjustment of the pulp flow rate in line 84

(iii) the flushing of pulp through supply portion 13 and mechanical outlet portion 11.

The adjustment of gap size is carried out, in part, by gap controller 166 which receives a signal, corresponding to the "gap size set point", from sequencer 156 via conductor 168. Gap controller 166 compares this "gap size set point" signal with another signal received from displacement transducer 58 via conductor 170, corresponding to the "measured gap size".

This "measured gap size" signal is also conveyed to display recorder 160 via conductor 172 for recording of the gap size.

An inequality between the "gap size set point" and the "measured gap size" signal causes gap controller 166 to convey a signal via conductor 174 to motor 54 to adjust the size of gap 34.

The adjustment of pulp flow rate is carried out, in part, by flow controller 176 which receives a signal corresponding to a temperature corrected "flow rate set point", conveyed by temperature correction module 178 via conductor 180. It should be mentioned here that temperature correction module 178 receives a signal corresponding to the "flow rate set point" from sequencer 156 via conductor 182 and corrects the signal with regard to the temperature of the pulp. For this, temperature correction module 178 also receives a signal from temperature transmitter 184, joined to line 84, via conductor 186.

In this case, the flow rate set point is increased in response to an increase in temperature of the pulp and is done so according to a fixed function. If, however, the temperature variation is small (for instance a variation of approximately 2° C. from the temperature at calibration), then the correction may be made proportional thereto.

Returning now to flow controller 176, a signal corresponding to the "measured flow rate" is received via conductor 188 from flow transmitter 190 which is placed in line 84. This "measured flow rate" signal is also conveyed to display recorder 160 via conductor 192 for recording the flow rate. An inequality of the temperature corrected "flow rate set point" signal and the "measured flow rate" signal causes flow controller 176 to convey a signal via conductor 194 to speed controller 116a of motor 116 to adjust the flow rate through line 84.

Finally, to initiate the flushing of pulp, sequencer 156 is coupled to solenoid 132a via conductor 195 for actuating supply valve 132 thereby opening line 134, 136 and delivering pulp from supply line 130 to agitation tank 120.

Also coupled to sequencer 156 is solenoid 128a via conductor 196 for actuating drain valve 128 thereby opening line 126 and draining pulp from agitation tank 120.

If supply pipe lines 144 and 152 are also linked to agitation tank 120, then solenoids 138a and 146a may be coupled to sequencer 156 by use of conductors 198 and 200 respectfully.

Also contemplated is the coupling of sequencer 156 to release solenoid 96 by means of conductor 202 to manually actuate release valve 100 and thereby cylindrical cup 18.

If desired, a computer equipped with the necessary input-output interfaces may replace the automatic control portion 12. In this instance, the computer receives signals from each of:

(i) level switch 94 via conductor 98, 153

(ii) displacement transducer 58 via conductor 170

(iii) flow transmitter 190 via conductor 188

(iv) temperature transmitter 184 via conductor 186 and issues outputs to each of:

(i) motor 54 via conductor 174

(ii) pump motor 116 via conductor 194

(iii) supply valve 132 and drain valve 128 via conductors 195 and 196 respectively The computer may follow a preset routine to count the impedances, adjust the gap size and flow rate while correcting same for temperature variations in the pulp. The accumulated data may be stored in a suitable memory or be recorded on a printer or plotter as is known.

The apparatus is calibrated using water. For each gap size, the flow rate of water at a given temperature is adjusted until at a constant flow rate, the column of water remains at a constant fixed equilibrium height. This combined gap size/flow rate calibration data is then used when setting up the input parameters for the analysis of wood pulp.

At the onset of on-line monitoring of the shive size distribution, all system input parameters are entered into the sequencer 156 by means of input panel 164. These parameters include:

(i) the gap set points for gap controller 166

(ii) the flow set points for flow controller 176

(iii) the impedance count time interval for each gap and flow combination (iv) the sequence for actuating the supply and drain valves.

Following the input of these variables, the operator enters the start-up command on the input panel 164, which causes the following events:

(a) Valve 100 is actuated to upwardly release cylindrical cup 18.

(b) Valve 132 is actuated thereby opening line 134, 136 to cause the passage of wood pulp therethrough from supply line 130 to fill agitation tank 120.

(c) Sequencer 156 conveys the first gap set point to gap controller 166 which, in turn, actuates motor 54 which rotates the annular ring 50 to set the first gap size at which impedance counting will be carried out.

(d) sequencer 156 conveys the first flow rate set point to flow controller 176 via temperature correction module 178. In turn, flow controller 176 signals speed controller 116a to adjust the flow rate of pump 114.

(e) Agitator 122 is actuated via conductor 124 for mixing the pulp in the agitation tank 120 and remains in operation throughout the monitoring procedure.

The flushing sequence follows wherein the wood pulp proceeds through pump 114 and is directed to the stand-pipe 70, via line 84. The wood pulp then enters closure chamber from stand-pipe 70 via line 14 and passes by spherical plug 32 and finally through the closure assembly outlets 40b. Following this, the wood pulp enters the pulp collection reservoir 41 and is directed through reservoir outlet 41a where return line 42 directs the pulp to agitation tank 120. From here, the wood pulp enters either line 118 to be recirculated, or drain line 126 or overflow line 125, to be discarded.

Immediately following the flushing sequence, sequencer 156 initiates the following operations:
(a) Cylindrical cup 18 is repositioned to form gap 34 at the preset maximum gap size by actuating release valve 100.
(b) Supply valve 132 is actuated to close line 134, 136 after an adequate sample of pulp has been collected from supply line 130.
(c) Drain valve 128 is actuated to close line 126 and maintain the pulp sample.
(d) Counter 152 is reset to begin counting.

At this point, the column of pulp in stand-pipe 70 begins to rise toward a fixed equilibrium height which is determined by calibration with water, and is sensed by low height sensing electrode 86. As the wood pulp passes through gap 34, a portion of the shives having a size greater than that of the gap, is temporarily prevented from passing therethrough. This impedance of over-sized shives causes a reduction in the flow rate through the gap while the flow rate of pump 114 remains constant.

As a result, the height of the column of pulp in standpipe 70 increases beyond a maximum height corresponding to an impedance threshold level, which is sensed by the high height sensing electrode 88. Immediately thereafter, release valve 100 is actuated to quickly release cylindrical cup 18, thereby permitting the over-sized shives past the plug 32. The speed of this release may be governed, in part, by the displacement of adjusting screw 66 and the pressure in pneumatic line 102.

Following the release of the impedance, the column of pulp lowers until it reaches the fixed equilibrium height and therefor low height sensing electrode 86 whereby cylindrical cup 18 is then automatically repositioned to form gap 34, which consequently increases the impedance count by 1, in counter 152.

It should be noted that the first cylindrical cup release for a given gap size is a function of both the impedance and the rising level of pulp in the standpipe. Consequently, counter 152 is reset after the first one to five counts, thereby starting the impedance count.

At the end of the impedance count interval, the sequencer 156 resets counter 152 and initiates the following results:
(a) Display recorder 160 records:
  (i) the impedance count
  (ii) the flow rate through line 84
  (iii) the size of gap 34
  (iv) the temperature of the pulp in line 84
(b) Motor 54 is automatically activated by gap controller 166 following a set point signal conveyed by sequencer 156 thereto, to adjust the size of gap 34.
(c) The flow rate of pump 114 is automatically adjusted in response to a set point signal to flow controller 176.

With the gap at its adjusted size, the impedance counting is repeated over the impedance count interval, with the impedance count, the corresponding adjusted gap size, flow rate and pulp temperature recorded thereafter.

The automatic shive analyzer continues in this manner until an impedance count for each gap size set point is recorded. Upon completion thereof, the flushing sequence is automatically initiated and, if desired, the monitoring procedure repeated thereafter with another pulp sample from supply line 130. Finally, the results of the impedance counts at each gap size set point may be interpreted as a size distribution of the shives in the pulp.

The following examples will serve to illustrate the shive size distribution analysis provided by the invention and the consistency of the data delivered with existing manual shive content techniques.

EXAMPLES 1–5

Five pulp examples were chosen from 5 separate homogeneous pulp sources. Each was analyzed by means of a mini shive apparatus, having a vibrating screen as is known to those skilled in the art, to determine the "Debris Content" in each sample.

Debris Content is a measurement of the percentage, in the pulp, of shives and other material that require further treatment to produce the highest grade of paper. In other words, the quality of pulp varies inversely with the debris content thereof.

For instance, examples 1, 2 and 3 were extracted from three unique sources of refined rejected pulp, each being homogeneously mixed. Example 1, represented by circles in FIG. 4, had a Debris Content of 1.5 percent. Example 2, represented by triangles in FIG. 4, had a Debris Content of 3.4 percent. Example 3, represented by squares in FIG. 4, had a Debris Content of 5.1 percent.

Figure 4:
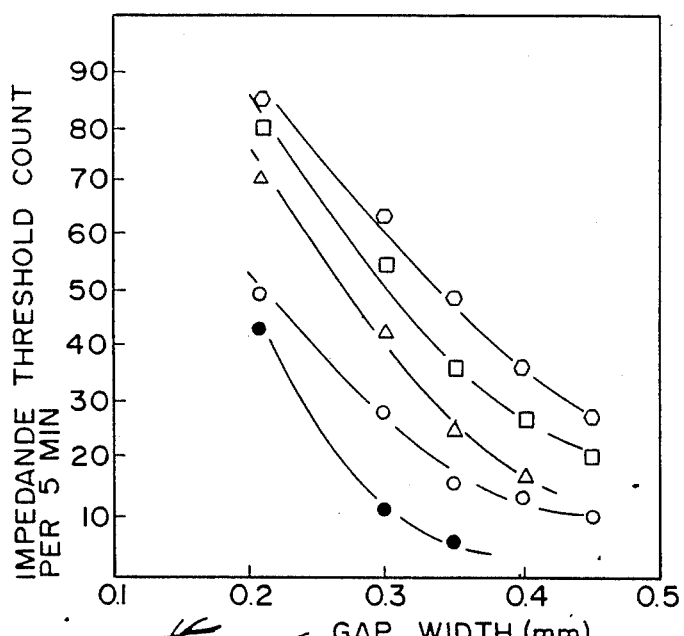
FIG. 4 is a diagram illustrating the number of counts of impedances during five minute intervals (ordinate) with respect to the size of the gap (abscissa) for several pulp samples.

Example 4, represented by pentagons in FIG. 4, was an unrefined rejected pulp and had a Debris Content of 8.5 percent.

Example 5, represented by solid circles in FIG. 4, was a filtered pulp and had a Debris Content of 1.5 percent.

Each example was analyzed by the automatic shive analyzer with impedance count interval preset at 5 minutes.

As can be seen in FIG. 4, the impedance threshold count increased with reduced gap size. Furthermore, the impedance threshold counts were found to vary directly with the Debris Content. Therefore the results are consistent with the Debris Content as was predicted.

Having described the invention comprising a method and an apparatus to obtain automatically the size distribution of shives, other numerous, modifications will be evident to those skilled in the art without departing from the spirit of the invention, as defined in the appended claims.

I claim:

1. An apparatus to automatically determine, on-line, the shive content and shive size distribution of a wood pulp containing shives, said apparatus comprising:
a line having an inlet for receiving a flow of wood pulp containing shives and an outlet whereby said flow of pulp is leaving said line,
a plugging means for closing said line,
a means to automatically actuate said plugging means, as to define a gradually increasing or decreasing gap in said plugging means,
and responsive to said means automatically actuating said pluggins means, a means translating and recording the size of said gap, said gap allowing during operating conditions the passage of the flow of wood pulp and the portion of shives having less than the size of said gap at a given moment, while temporarily preventing the passage of shives exceeding the size of said gap and thereby interfering with the flow of wood pulp through the gap and thereby through said line, thereby causing impedance in said line, a means for sensing the impedance in said line over a predetermined impedance threshold level, and responsive to said means of sensing impedance over said threshold level a means for rapidly releasing said plugging means whereby upon each occurence of said impedance over said predetermined threshold level, said impedance sensing means actuates said rapidly releasing means and thereby instantaneously enlarge said gap from said operating conditions as to permit the passage threthrough of said shives exceeding the size of the gap, and a short period of time thereafter, rapidly returning said plugging means and said gap to said operating conditions, and responsive to said rapidly releasing means, a means for registering said occurrence of said impendance over said threshold level for said gradually increasing or decreasing gap during a predetermined period of time, a means responsive to said registering means and said means for translating and recording the gap size, to correlate the count of said occurrence to the size of said gap to automatically determined on-line the size distribution of said shive, and a means to deliver a constant flow of wood pulp in said inlet of said line, said means to deliver a constant flow being selected from the group comprising pressure measuring means, volume measuring means, pressure regulating means, volume regulating means.

2. An apparatus, as defined in claim 1, wherein said plugging means for closing said line is a plug and at least one displaceable wall disposed therearound, said actuating means is a guiding rod connected to said at least one displaceable wall and aligning said at least one displaceable wall with said plug and to displace said at least one displaceable wall with respect to said plug, to form said gradually increasing or decreasing gap, defined by the surface of said plug and the inner face of said at least one displaceable wall, and a threaded portion for engaging a rotational drive source with said guiding rod.

3. An apparatus as defined in claim 2 wherein said means translating and recording the size of said gap is a transducer device, operatively responsive to said guiding rod and thereby responsive to the actuation of said plugging means defining said gap.

4. An apparatus as defined in claim 1 wherein said means to deliver a constant flow of pulp adjusts the flow rate produced by said means to feed in said pulp, and is responsive to changes in the size of said gap.

5. An apparatus as defined in claim 1, wherein said means to deliver a constant flow of pulp generates a flow of pulp at a substantially constant flow rate in said line, and wherein said impedance causes an increase in pressure in excess of a predetermined value thereby defining said impedance threshold level, said means sensing impedance being responsive to pressures in said line in excess of the predetermined threshold level value.

6. An apparatus as defined in claim 1 wherein said line is substantially vertical, and includes the inlet on top of the line and the outlet at the bottom, thereby allowing for a column of pulp above said inlet so that the height of said column of pulp is indicative of impedance caused by the interference at the gap, whereby the height of said column of pulp increases until said impedance threshold level is exceeded, said means sensing impedance is responding to the height in excess of a predetermined height of said column of pulp.

7. An apparatus as defined in claim 1, wherein said means to deliver a constant flow of wood pulp is operatively coupled to said line inlet, for generating a flow of pulp at a substantially constant pressure in said line, wherein said impedance causes a decrease in flow rate below a predetermined minimum value, thereby defining said impedance threshold level, said sensing means being responsive to flow rates in said line below said predetermined minimum value.

8. The apparatus as defined in claim 1 wherein the temperature of the wood pulp delivered into said inlet is subject to variation, and wherein said means to deliver a constant flow of wood pulp, includes a wood pulp temperature measuring means.

9. A method for automatically determining on-line, the shive content and shive size distribution of a wood pulp containing shives, comprising:

(a) allowing a flow of water into a passage, (b) causing a gap in said passage, (c) automatically measuring said gap, (d) determining the rate of flow of water into said passage, for said flow of water to remain pressure and volume constant at a given water temperature and measuring said rate of flow, (e) registering the measured gap of step c) versus the measured rate of flow of water at said given water temperature of step d), (f) repeating step b) in causing different gaps in said passage and repeating thereafter for each of said different gaps, steps c) d) and e) in order to establish the relationship between definite gaps and their respective flow rates for water at said given water temperature, said flow rates to be delivered at constant volume and pressure, (g) causing a first given restraining gap in said passage, and automatically measuring said restraining gap, allowing a constant flow of wood pulp into said passage, at a rate equivalent to the flow rate for water established in step f) for said restraining gap and for water at substantially the same temperature as the wood pulp, and then sensing in said flow of wood pulp a differential: pressure differential when volume is constant and volume differential when pressure is constant, said differential resulting from interference in said flow of wood pulp caused by the shives exceeding the size of said restraining gap, (h) at a predetermined differential releasing said restraining gap in step g), (i) a short period of time thereafter, rapidly returning to said restraining gap, (j) repeating steps g), h) and i) during a predetermined period of time, counting the restraining gap releases, (k) registering the frequency at which said restraining gap is released over time, versus the measured restraining gap of said passage, (l) repeating steps g) h) i) j) and k) in causing restraining gaps different from said first, m) whereby automatically registering said frequency of step k) versus the different restraining gaps, automatically establishes on-line the shive content and shive size distribution of said wood pulp.

10. The method as defined in claim 8 wherein the temperature of the wood pulp allowed into said passage is subject to variation, and wherein the flow rate and the gap are translated in relation to said temperature variation.

* * * * *